United States Patent [19]

Nishimura et al.

[11] Patent Number: 5,912,146
[45] Date of Patent: Jun. 15, 1999

[54] METHOD FOR SYNTHESIS OF NUCLEIC ACIDS

[75] Inventors: Naoyuki Nishimura; Reiko Yoshida, both of Kyoto, Japan

[73] Assignee: Shimadzu Corporation, Kyoto, Japan

[21] Appl. No.: 08/911,735

[22] Filed: Aug. 15, 1997

[30] Foreign Application Priority Data

Sep. 9, 1996 [JP] Japan ................................. 8-238113

[51] Int. Cl.$^6$ .............................. C12P 19/34; C12N 9/28
[52] U.S. Cl. ....................... 435/91.1; 435/91.2; 435/202
[58] Field of Search .................................. 435/91.1, 91.2, 435/202

[56] References Cited

U.S. PATENT DOCUMENTS 5,618,665  4/1997  Lurie et al. .................................. 435/4
5,620,869  4/1997  Woodard et al. ....................... 435/91.1

*Primary Examiner*—Kenneth R. Horlick
*Assistant Examiner*—Joyce Tung

*Attorney, Agent, or Firm*—Nikaido, Marmelstein, Murray & Oram LLP

[57] ABSTRACT

The present invention provides a method of nucleic acid synthesis capable of directly amplifying a gene of interest in a salivary sample without purifying DNAs from the sample.

According to the present invention, in a method of nucleic acid synthesis by mixing a salivary sample itself and a gene amplification reaction solution, and then subjecting them to an amplification reaction, the salivary sample is heat-treated or treated with a saccharide-degrading enzyme before the reaction. For example, a salivary sample was heat-treated at 0–40° C. for 1 hour, subsequently added directly into a PCR reaction solution, and then subjected to a PCR. The result demonstrates that, as shown in FIG. 3, the amount of the PCR product increased according as the heat-treatment temperature was elevated, and as a consequence, the PCR product sufficient to be detected in the electrophoresis was produced in each of all cases using different amounts of saliva, by heat-treating the sample at 30° C. or above.

11 Claims, 2 Drawing Sheets

FIG. 3
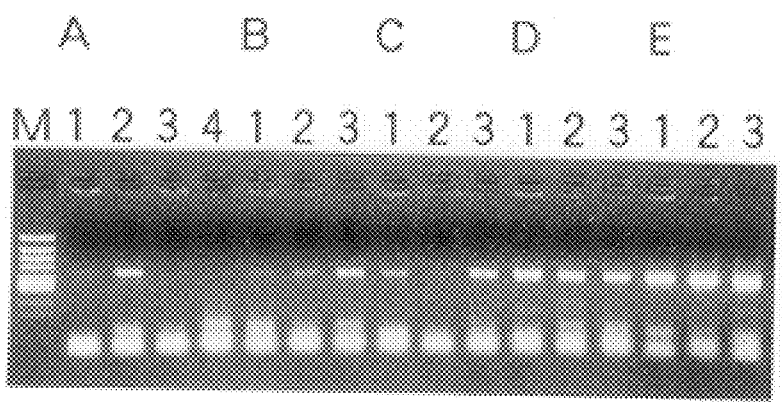
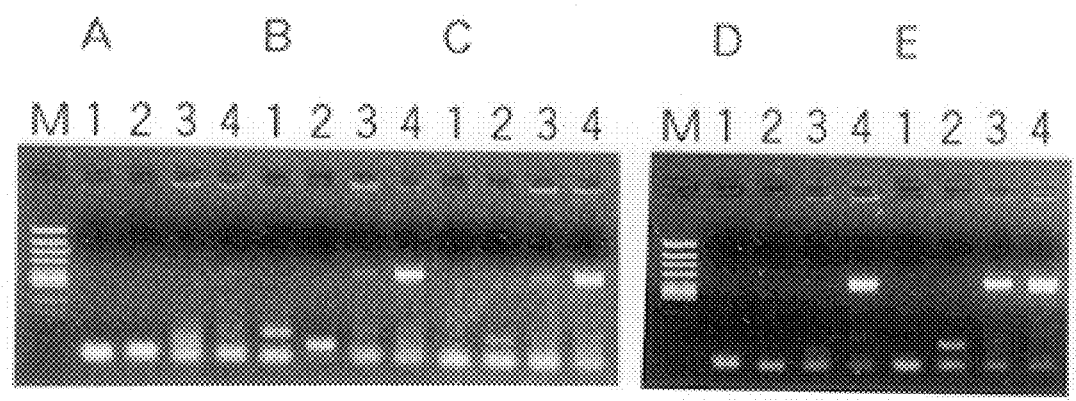
FIG. 4

METHOD FOR SYNTHESIS OF NUCLEIC ACIDS

BACKGROUND OF THE INVENTION

1. Field of the Invention

The present invention relates to a method for synthesis of nucleic acid. In particular, it relates to a method for synthesis of nucleic acid by means of Polymerase Chain Reaction (referred hereinafter as "PCR").

2. Description of the Prior Art

PCR is a method for amplifying a DNA fragment of interest by a factor of hundreds of thousands, in which primers are allowed to bind to a DNA so that a specific region within the DNA is located between the bound primers, then treated with a DNA polymerase, and such a DNA synthesis reaction is repeated. A PCR method is described in Japanese Laid-open Patent Publication No. 61-274697 (1986) of Mullis et al.

A PCR method can be used as a sensitive analysis of nucleic acids in various samples, especially derived from animal body fluids. Thus, a PCR method is used in, for example, diagnosing infections, hereditary diseases or cancers. PCR is also suitable for DNA typing in transplantation or judgement of parenthood. In such cases, peripheral blood is often used as a test material.

A disadvantage of PCR resides in that pigments, proteins, saccharides or unknown impurities inhibit the reaction. Actually, action of many of DNA polymerases, including Taq DNA polymerase, a typical thermostable DNA polymerase derived from Thermus aquaticus, have been well known to be strongly inhibited by a trace of body fluid-derived impurities in a PCR mixture.

Therefore, a PCR method requires an extraction of nucleic acids, before the DNA amplification, from cells, bacteria, viruses or the like (referred generically hereinafter as "gene inclusions") isolated from the subject to be tested. In order to eliminate any inhibitions, the gene inclusions are conventionally lysed by using, for example, enzymes, surfactants or chaotropic agents, and DNAs are then extracted from the lysed gene inclusions by using, for example, phenol or phenol-chloroform.

In recent years, ion exchange resins, glass filters or reagents having a protein-aggregating effect are often used in nucleic acid purification.

It is difficult, however, to remove impurities completely from the samples by these nucleic acid purification procedures. Furthermore, the recovery-quantity of nucleic acids from a sample often varies in these purification procedures. For these reasons, a subsequent nucleic acid synthesis may not sometimes work well, especially when the content of the nucleic acid of interest in the sample is low. In addition, these purification procedures are complicated and time-consuming, and are in danger of contamination.

Thus, a simpler and more effective method for pretreating samples for PCR are required in order to overcome these problems.

Although peripheral blood is often used as a test material for a gene examination, mucous membrane cells of the mouth cavity are superior to peripheral blood as a test material because of their easiness in sampling and the lower risk of infection.

In order to extract DNAs from mucous membrane cells of the mouth cavity, such cells scraped off the mouth cavity with a brush or the like are conventionally treated with a proteolytic enzyme, and DNAs are then purified by means of any one of the above mentioned purification procedures. As mentioned above, however, these procedures have many problems including those in quality and quantity of the DNAs recovered (e.g. an incomplete removal of impurities or a variation in the amount of recovered DNAs) as well as difficulty in treating multiple samples due to the complexity of the procedures, the time-consuming manipulation and the high risk of contamination during the procedures.

SUMMARY OF THE INVENTION

Thus, it is an object of the present invention to provide a new method of nucleic acid synthesis capable of directly amplifying a gene of interest in saliva. In other words, it is an object of the present invention to provide a method in which salivary DNAs are used in a nucleic acid synthesis without purifying them from saliva.

The present inventors have first found that, when saliva was used as a sample, the amplification efficiency of PCR, which is typically low, was increased by the storage of the sample at a low temperature (e.g. 5° C.) for prolonged time. Secondly, the inventors have also found that, when the salivary samples were heat-treated at various temperatures before adding them into PCR reaction solutions, the amplification efficiency increased according as the temperature of the heat-treatment was elevated and according as the duration of the heat-treatment was prolonged.

On the other hand, it is well known that DNAs purified from blood which has been treated with a saccharide, heparin, highly inhibits the PCR.

From these observations, we have speculated that major materials in saliva responsible for the PCR inhibition may be some saccharides and that degrading enzymes in saliva may have degraded such inhibitory saccharides during the storage of the samples, resulting in the increased efficiency of the PCR.

Finally, we have found that, when saliva was pretreated, before use in a PCR, with amylase, one of saccharide-degrading enzymes, the PCR inhibitory materials in saliva were degraded in shorter time at lower temperature compared to those without the amylase pretreatment. Thus, the present invention has been accomplished.

That is, the present invention is to use salivary DNAs in a nucleic acid synthesis without purifying them from saliva.

To this end, the present invention provides methods for degrading the saccharides in saliva responsible for the PCR inhibition. A heat-treatment of saliva is one of such methods.

Thus, the first aspect of the present invention includes a method for synthesis of nucleic acid by mixing a salivary sample itself and a gene amplification reaction solution, and then subjecting them to an amplification reaction, which comprises heat-treating the salivary sample before the reaction.

In this method, the temperature of the heat-treatment is preferably 30° C. or above, and the duration of the heat-treatment is preferably 10 minutes or longer.

Furthermore, a treatment of saliva with a saccharide-degrading enzyme is also one of methods for degrading the saccharides in saliva responsible for the PCR inhibition.

Thus, the second aspect of the present invention includes a method for synthesis of nucleic acid by mixing a salivary sample itself and a gene amplification reaction solution, and then subjecting them to an amplification reaction, which comprises treating the salivary sample with a saccharide-degrading enzyme before the reaction.

In this method, the saccharide-degrading enzyme is preferably an amylase.

The preferred amount of the saccharide-degrading enzyme used is 0.01–0.1 units per μl of the salivary sample.

The present invention enables to synthesize a gene of interest efficiently even when a salivary sample is directly added into a reaction solution for nucleic acid synthesis. Therefore, the preparation of a sample containing nucleic acids for nucleic acid synthesis can be achieved simply and quickly.

BRIEF DESCRIPTION OF THE DRAWINGS

FIG. 3 shows the gel-electrophoresed product of a PCR in which a salivary sample was incubated at 0–40° C. for 1 hour, subsequently directly added into a PCR reaction solution, and then subjected to a PCR.

FIG. 4 shows the gel-electrophoresed product of a PCR in which a salivary sample was incubated at 0–40° C. for 10 minutes in the absence of or in the presence of added α-amylase derived from human, subsequently directly added into a PCR reaction solution, and then subjected to a PCR.

DETAILED DESCRIPTION OF THE INVENTION

Figures 1, 2:
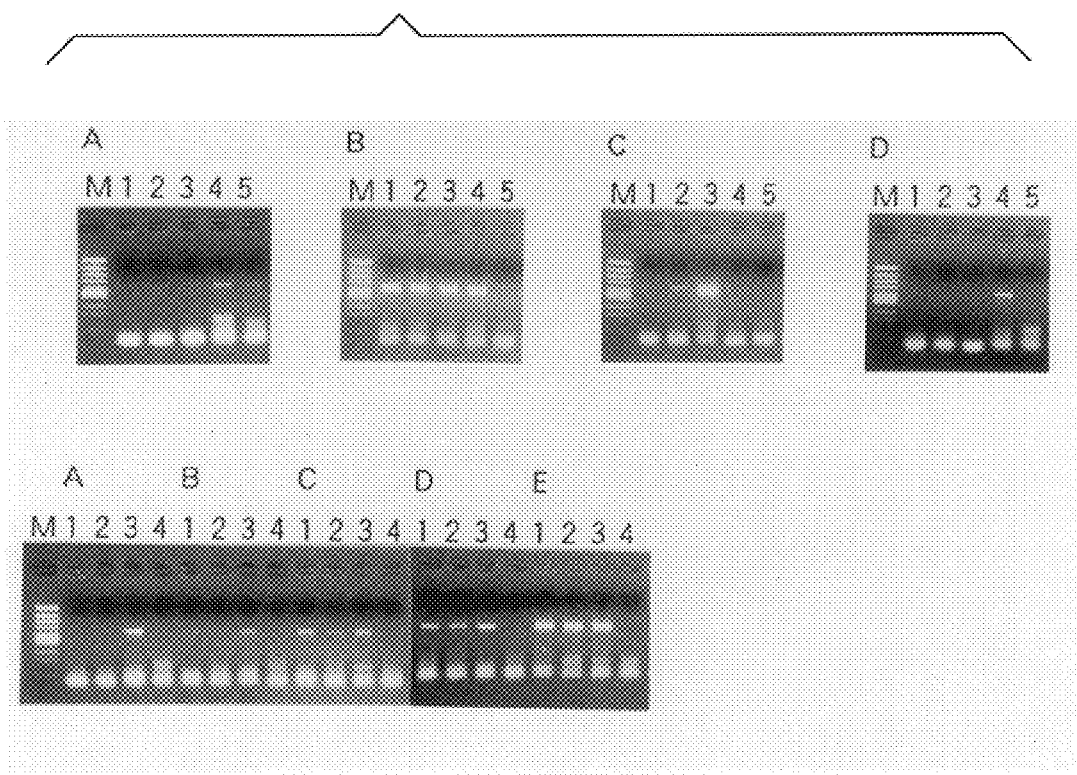
FIG. 1 shows the gel-electrophoresed product of a PCR in which a salivary sample was directly added, before or after storage at various temperatures, into a PCR reaction solution, and then subjected to a PCR.
FIG. 2 shows the gel-electrophoresed product of a PCR in which a salivary sample was incubated at 37° C. for 0–120 minutes, subsequently directly added into a PCR reaction solution, and then subjected to a PCR.

The first aspect of the present invention includes a method for synthesis of nucleic acid by mixing a salivary sample itself and a gene amplification reaction solution, and then subjecting them to an amplification reaction, which comprises heat-treating the salivary sample before the reaction.

The term "salivary sample" refers to a saliva itself or a dilution of saliva. Although the heat-treatment "before the reaction" may be done before or after admixing a salivary sample with a PCR reaction solution, it is preferable to heat-treat a salivary sample alone before admixing with a PCR reaction solution. When a salivary sample is to be heat-treated after admixing with a PCR reaction solution, it is necessary to select appropriate primers in order not to increase non-specific amplification products such as a primer dimer. In these cases, such an increase in the amount of non-specific amplification products may be inhibited by repressing the activity of a DNA polymerase by using, for example, antibodies against the polymerase. Alternatively, a salivary sample may be directly added into a PCR reaction solution lacking a part thereof (such as a DNA polymerase or primers), followed by a heat-treatment, and then the lacking part is added thereto in order for inhibiting an increase in the amount of non-specific amplification products.

The preferred temperature for the heat-treatment is 30° C. or above. Typically, the upper limit of the temperature for the heat-treatment is about 90° C. The preferred duration of the heat-treatment is more than 10 minutes, preferably more than 30 minutes, further preferably 60–120 minutes. In our studies, for example, the PCR inhibition was eliminated by treating a salivary sample at 40° C. for about 10 minutes, while an treatment at 5° C. required several days in order to eliminate the PCR inhibition.

The second aspect of the present invention includes a method for synthesis of nucleic acid by mixing a salivary sample itself and a gene amplification reaction solution, and then subjecting them to an amplification reaction, which comprises treating the salivary sample with a saccharide-degrading enzyme before the reaction.

In this method, the saccharide-degrading enzyme is preferably an amylase.

The saccharide-degrading enzymes include, for example, but not limited to, α-amylase, β-amylase, exo-1,4-α-D-lucosidase, cellulase, endo-1,3(4)-β-D-glucanase, inulinase, endo-1,4-β-D-xylanase, oligo-1,6-glucosidase, dextranase, chitinase, polygalacturonase, lysozyme, neuraminidase, α-D-glucosidase, β-D-glucosidase, α-D-galactosidase, β-D-galactosidase, α-D-mannosidase, β-D-mannosidase, β-D-fructofuranosidase, α-α'-trehalase, α-N-acetyl-D-glucosaminidase, β-D-glucuronidase, endo-1,3- β-D-xylanase, amylo-1,6-glucosidase, hyaluronoglucosaminidase, hyaluronoglucuronidase, exo-1,4-β-D-xylosidase, β-D-fucosidase, endo-1,3-β-D-glucanase, α-L-rhamnosidase, pullulanase, GDP glucosidase, β-L-rhamnosidase, fucoidanase, glucosylceramidase, galactosylceramidase, galactosylgalactosylglucosylceramidase, sucrose α-glucohydrolase, α-N-acetyl-D-galactosaminidase, α-N-acetyl-D-glucosaminidase, α-L-fucosidase, β-N-acetyl-D-hexosamididase, β-N-acetyl-D-galactosaminidase, cyclomaltodextrinase, α-L-arabinofuranosidase, glucuronosyl-disulfoglucosamine glucuronidase, isopullulanase, exo-1,3-β-D-glucosidase, endo-1,3-α-D-glucanase, exo-maltotetrahydrolase, mycodextranase, glycosylceramidase, 1,2-α-L-fucosidase, 2,6-β-D-fructanase, 6-levanbiohydrolase, levanase, quercitrinase, exopolygalacturonase, isoamylase, exo-1,6-α-D-glucosidase, endo-1,2-β-D-glucanase, exo-1,3-β-D-xylosidase, lichenase, exo-1,4-β-D-glucosidase, endo-1,6-β-D-glucanase, L-iduronidase, exo-1,2-1,3-α-D-mannosidase, endo-1,4-β-D-mannanase, exo-β-D-fructosidase, agarase, exo-poly-α-D-galacturonosidase, κ-carrageenanase, exo-1,3-α-glucanase, oligogalacturonate lyase, heparin lyase, heparitin sulfate lyase, exopolygalacturonate lyase, pectin lyase, threonine synthase.

The amount of the saccharide-degrading enzyme added is preferably 0.01–0.1 units per 1 μl of the saliva sample. In our studies, for example, the PCR inhibition was eliminated by pretreating 5 μl of human saliva, collected by holding 1% NaCl in the mouth, with 0.5 unites of human amylase at 10° C. or above for 10 minutes. On the contrary, when the same saliva was heat-treated in the absence of amylase for 10 minutes, a treatment at 40° C. was required for achieving the equivalent effect.

The PCR reaction solution used in the present invention typically contains pH buffers, salts such as $MgCl_2$ or KCl, primers, deoxyribonucleotides, and a DNA polymerase. The salts mentioned above may be substituted with other salts, if necessary. In addition, a variety of other materials, including dimethylsulfoxide, surfactants such as Nonidet P-40 or polyoxyethylenesorbitan, and proteins such as gelatin or albumin, may be included.

A preferred pH buffer used in the present invention is a combination of tris(hydroxymethyl)aminomethane and a mineral acid such as hydrochloric acid, nitric acid or sulfuric acid, hydrochloric acid being preferred among the mineral acids. A variety of other pH buffers may also be used, including a combination of Tricine, CAPSO (3-N-cyclohexylamino-2-hydroxypropanesulfonic acid) or CHES (2-(cyclohexylamino)ethanesulfonic acid) and sodium hydroxide or potassium hydroxide.

A pH-adjusted buffer is used in the PCR reaction solution at a concentration in the range of 10 mM to 100 mM.

The term "primer" used herein refers to an oligonucleotide acting as a starting point from which the synthesis begins in the presence of a DNA, reagents for polymerization and so on. Although a primer is preferably single-stranded, double-stranded primers may also be used. When double-stranded primers are used, it is desirable to convert them into their single-stranded forms before use in an amplification reaction.

Primers may be synthesized using well known methods, or may be isolated from organisms.

The term "polymerase" means an enzyme which catalyzes a nucleic acid synthesis via a primer binding or such a chemical synthesis system. Suitable polymerases include, but not limited to, DNA polymerase I derived from *E. coli*, the Klenow fragment of DNA polymerase derived from *E. coli*, T4 DNA polymerase, Taq DNA polymerase, *T. litoralis* DNA polymerase, Tth DNA polymerase and Pfu DNA polymerase.

EXAMPLES

Example 1

This example describes a study in which a salivary sample, exhibiting a low PCR efficiency when added directly into a reaction solution, was stored at 5° C., -20° C. or -80° C. for 12 days, and then used directly in a PCR.

Human saliva collected by rinsing out the mouth with 10 ml of 1% NaCl was used as a test material. Various amounts of the sample were directly added into PCR reaction solutions in the total volume of 50 μl, and then subjected to PCRs. The PCR reaction solution used contained 10 mM Tris-HCl adjusted to pH 9.2, 50 mM KCl, 1.5 mM $MgCl_2$, 200 μM of dATP, dCTP, dGTP, and dTTP, 1.0 μM primers, 2.5 units/100 μl Taq DNA polymerase (TaKaRa Taq; Takara shuzo, Kyoto, Japan).

The primers used in the PCR were an oligonucleotide having a base sequence of the plus strand (P1) located within the human beta-globin coding region and an oligonucleotide having a base sequence of the minus strand (P2) located within that region, and these primers may produce a 408 bp amplification product by PCR (Saiki, R. K., Gelfand, D. H., Stoffel, S., Scharf, S. J., Higuchi, R., Horn, G. T., Mullis, K. B. and Erlich, H. A. (1988) Science 239, 487–491).

P1: 5' GAA GAG CCA AGG ACA GGT AC 3' (SEQ ID NO:1)

P2: 5' GGA AAA TAG ACC AAT AGG CAG 3' (SEQ ID NO:2)

The PCR was achieved by pre-heating at 94° C. for 2 minutes followed by 40 cycles of polymerization at 94° C. for 1 minute, at 55° C. for 1 minutes, and then 72° C. for 1 minutes, and finally polymerization at 72° C. for 7 minutes. After the PCR was completed, 5 μl of the reaction solution was electrophoresed on a 3% agarose-TAE (40 mM Tris-acetate, 1 mM EDTA, pH 8.0) gel containing 0.5 μg/ml ethidium bromide, and detected.

FIG. 1 shows the electrophoresed product of a PCR in which the salivary sample was directly added, before or after storage, into the PCR reaction solution, and then subjected to a PCR. In the Figure, panel A shows the electrophoresed PCR product obtained by directly using the salivary sample without storage, and panels B, C and D show the electrophoresed PCR product obtained by directly using the salivary sample after storage at 5° C., -20° C. or -80° C., respectively, for 12 days. The lanes 1–5 in the Figure correspond to the results obtained by adding 4 μl (lane 1), 2 μl (lane 2), 1 μl (lane 3), 0.5 μl (lane 4) or 0 μl (lane 5) of the salivary sample, respectively. Lane M shows molecuar weight markers (φ×174 RF DNA digested with a restriction enzyme, HinC II).

As can be seen from panel A in the Figure, when the present salivary sample was directly used in a PCR immediately after its collection, only a trace of the PCR product was detected in lane 4, indicating that the present saliva had a strong inhibition effect on PCR.

Panels B, C and D show the result obtained by using the present salivary sample which has been stored at 5° C., -20° C. or -80° C., respectively, for 12 days before directly used in the PCRs. On panel C, in which the salivary sample was stored at -20° C., large amount of the PCR product was detected in lane 3, while lane 2 exhibited only a trace of the product, and lanes 1 and 4 didn't exhibit any PCR products. On panel D, in which the salivary sample was stored at -80° C., only lane 4 exhibited a small amount of the PCR product. On the contrary, a large amount of the PCR product was detected in each lane on panel B in which the salivary sample was stored at 5° C.

Example 2

This example describes a study in which a salivary sample was heat-treated at 37° C. for 0–120 minutes, and then used directly in a PCR. The sample was saliva collected by using the same procedure as that in Example 1. The composition of the PCR reaction solution, and the conditions of the PCR and the electrophoresis after the PCR were also the same as in Example 1.

FIG. 2 shows the electrophoresed product of a PCR in which the heat-treated salivary sample was directly added into a PCR reaction solution. Panels A–E in the Figure correspond to the results obtained by heat-treating the salivary samples for 0 minute (panel A), 15 minutes (panel B), 30 minutes (panel C), 1 hour (panel D) and 2 hours (panel E), respectively. Lanes 1–4 correspond to the results obtained by adding 4 μl (lane 1), 2 μl (lane 2), 1 μl (lane 3) and 0 μl (lane 4) of the saliva sample, respectively. Lane M is the same markers as in Example 1. These results indicate that the amount of the PCR product increased according as the time of the heat-treatment was prolonged.

Example 3

This example describes a study in which a salivary sample was heat-treated at 0–40° C. for 1 hour and then used directly in a PCR. The sample was saliva collected by using the same procedure as in Example 1. The composition of the PCR reaction solution, and the conditions of the PCR and the electrophoresis after the PCR were also the same as in Example 1.

FIG. 3 shows the electrophoresed product of a PCR in which a heat-treated salivary sample was directly added into the PCR reaction solution. Panels A–E in the Figure correspond to the results by heat-treating the salivary samples at 0° C. (panel A), 10° C. (panel B), 20° C. (panel C), 30° C. (panel D) and 40° C. (panel E), respectively. Lanes 1–4 correspond to the results obtained by adding 4 μl (lane 1), 2 μl (lane 2), 1 μl (lane 3) and 0 μl (lane 4) of the saliva sample, respectively. Lane M is the same markers as in Example 1. These results indicate that the amount of the PCR product increased according as the temperature of the heat-treatment was elevated, and as a consequence, the PCR product sufficient to be detected in the electrophoresis was produced in each of all cases using different amounts of saliva, by heat-treating the sample at 30° C. or above.

Example 4

This example describes a study in which the effect of pre-treatment of saliva with amylase on the PCR efficiency was examined. Five µl of saliva collected by using the same procedure as in Example 1 was used as the sample. The amylase used was α-amylase derived from human, and added 0.5 units per 5 µl of the salivary sample. The composition of the PCR reaction solution, and the conditions for the PCR and the electrophoresis after the PCR were the same as in Example 1.

After the amylase pre-treatment, the saliva sample was directly added into the PCR reaction solution, and subjected to a PCR. FIG. 4 shows the electrophoresed product of such a PCR. Panels A–E correspond to the results obtained by pre-treating the sample at 0° C. (panel A), 10° C. (panel B), 20° C. (panel C), 30° C. (panel D) and 40° C. (panel E), respectively, for 10 minutes. Lanes 1–4 correspond to the results obtained by adding nothing (lane 1), amylase (lane 2), saliva (lane 3) and saliva along with amylase(lane 4), respectively. Lane M shows the same markers as used in Example 1.

As shown in lane 3 on each of panels A–E, when saliva was used without the amylase pre-treatment, only the heat-treatment at 40° C. allowed to produce the PCR product sufficient to be detected in the electrophoresis. On the contrary, as shown in lane 4 on each of panels A–E, when saliva was pre-treated with amylase, all heat-treatments at 10° C. or above were enough to produce the PCR product sufficient to be detected in the electrophoresis. Furthermore, as shown in lane 2 on each of panels A–E, it was confirmed that the PCR product appeared concomitant with the amylase addition is not a carryover of DNA from human α-amylase used.

---

---

What is claimed is:

1. A method for the amplification of nucleic acids in a salivary sample, comprising (1) without pre-pretreating said salivary sample with any enzyme, acid, base or surfactant, treating said salivary sample consisting essentially of saliva with a polysaccharide-degrading enzyme to obtain a treated salivary sample;

(2) mixing the treated salivary sample and a gene amplification reaction solution to obtain a mixture; and thereafter (3) subjecting the mixture to an amplification reaction.

2. The method of claim 1, wherein the polysaccharide-degrading enzyme is an amylase.

3. The method of claim 2, wherein the amount of the polysaccharide-degrading enzyme used is about 0.01–0.1 units per µl of the salivary sample.

4. The method of claim 1, wherein the polysaccharide-degrading enzyme is α-amylase, β-amylase, gluco amylase, phosphorylase, pullulanase or isoamylase.

5. A method for the preparation of nucleic acids in a salivary sample, comprising (1) treating a salivary sample with a single polysaccharide-degrading enzyme to obtain a treated salivary sample, wherein said polysaccharide-degrading enzyme is α-amylase, β-amylase, gluco amylase, phosphorylase, pullulanase or isoamylase;

(2) mixing the treated salivary sample and a gene amplification reaction solution to obtain a mixture; and thereafter (3) subjecting the mixture to an amplification reaction.

6. The method of claim 5, wherein the polysaccharide-degrading enzyme is an amylase.

7. The method of claim 5, wherein the amount of the polysaccharide-degrading enzyme used is about 0.01–0.1 units per µl of the salivary sample.

8. A method for the amplification of nucleic acids in a salivary sample, comprising (1) treating said salivary sample consisting essentially of saliva with an agent consisting essentially of a polysaccharide-degrading enzyme to obtain a treated salivary sample;

(2) mixing the treated salivary sample and a gene amplification reaction solution to obtain a mixture; and thereafter (3) subjecting the mixture to an amplification reaction.

9. The method of claim 8, wherein the polysaccharide-degrading enzyme is an amylase.

10. The method of claim 8, wherein the amount of the polysaccharide-degrading enzyme used is about 0.01–0.1 units per µl of the salivary sample.

11. The method of claim 8, wherein the polysaccharide-degrading enzyme is α-amylase, β-amylase, gluco amylase, phosphorylase, pullulanase or isoamylase.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:1:

GAAGAGCCAA GGACAGGTAC      20

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

GGAAAATAGA CCAATAGGCA G      21